(12) United States Patent
Reetz et al.

(10) Patent No.: US 7,704,912 B2
(45) Date of Patent: Apr. 27, 2010

(54) MIXTURES OF CHIRAL MONOPHOSPHORUS COMPOUNDS USED AS LIGAND SYSTEMS FOR ASYMMETRIC TRANSITION METAL CATALYSIS

(75) Inventors: Manfred T. Reetz, Mülheim an der Ruhr (DE); Thorsten Sell, Frankfurt am Main (DE); Andreas Meiswinkel, Mülheim an der Ruhr (DE); Gerlinde Mehler, Mülheim an der Ruhr (DE)

(73) Assignee: Studiengesellschaft Kohle mbH, Molhelm an der Ruh (DE)

( * ) Notice: Subject to any disclaimer, the term of this patent is extended or adjusted under 35 U.S.C. 154(b) by 819 days.

(21) Appl. No.: 10/530,818

(22) PCT Filed: Sep. 26, 2003

(86) PCT No.: PCT/DE03/03226

§ 371 (c)(1),
(2), (4) Date: Apr. 8, 2005

(87) PCT Pub. No.: WO2004/035208

PCT Pub. Date: Apr. 29, 2004

(65) Prior Publication Data

US 2006/0014981 A1  Jan. 19, 2006

(30) Foreign Application Priority Data

Oct. 11, 2002  (DE) ............................... 102 47 633

(51) Int. Cl.
| | |
|---|---|
| *B01J 21/00* | (2006.01) |
| *B01J 23/00* | (2006.01) |
| *B01J 25/00* | (2006.01) |
| *B01J 29/00* | (2006.01) |
| *B01J 31/00* | (2006.01) |
| *B01J 27/00* | (2006.01) |
| *B01J 21/04* | (2006.01) |
| *B01J 23/02* | (2006.01) |

(52) U.S. Cl. ...................... 502/162; 502/100; 502/150; 502/208; 502/439; 502/506

(58) Field of Classification Search ................. 502/162, 502/100, 150, 208, 439, 506

See application file for complete search history.

(56) References Cited

U.S. PATENT DOCUMENTS 5,360,938 A  11/1994  Babin et al.

FOREIGN PATENT DOCUMENTS

WO  WO 01/94278 A  12/2001

OTHER PUBLICATIONS

Reetz et al.; Angew. Chem. Int. Ed. 2000, 39, (21), 3889-3890.*

Claver et al.; Chem. Commun., 2000, 961-962, as supplied by applicants.*

Chen W. et al: "Asymmetric activation of conformationally flexible monodentate phosphates for enantioselective hydrogenation"; Tetrahedron Letters, Elsevier Science Publishers, Amsterdam NL, vol. 42, No. 49, Dec. 3, 2001, pp. 8737-8740 XP004321537.

Database Registry Online CA, Registry No. RN 174367-22-7, Mar. 20, 1996 XP002271188.

Reetz M. T. et al.: "Mixtures of chiral and achiral monodentate ligands in asymmetric Rh-catalyzed olefin hydrogenation: reversal of enantioselectivity", Tetrahedron Letters, Elsevier Science Publishers, Amsterdam, NL, vol. 44, No. 24, Jun. 9, 2003, pp. 4593-4596 XP004425274.

Reetz M. T. et al.: "A new principle in combinatorial asymmetric transition-metal catalysis: mixtures of chiral monodentate P ligands", Angew. Chem. Int. Ed., vol. 42, No. 7, (2003) pp. 790-793 XP002270700.

Pena D., et al.: "Improving conversion and enantioselectivity in hydrogenation by combining different monodentate phosphoramidites; a new combinatorial approach in asymmetric catalysis" Org. Biomol. Chem., vol. 1 (2003) pp. 1087-1089 XP002270701.

Berg van den M et al: "Highly enantioselective Rhodium catalyzed hydrogenation with monodentate ligands" Journal of the American Chemical Society, American Chemical Society, Washington DC, US, vol. 122 No. 46, Nov. 22, 2000, pp. 11539-11540 XP002249650.

B. Cornils et al.; "Applied Homogeneous Catalysis with Organometallic Compounds A comprehensive Handbook in Two Volumes"; (1996); VCH Verlagsgesellschaft mbH, Weinheim, Germany.

W. S. Knowles et al; "Asymmetric Hydrogenations (Nobel Lecture)";The Nobel Prize in Chemistry 2001; (2002), pp. 1998-2007 Wiley-VCH Verlag GmbH, Weinheim, Germany.

R. Noyori; Asymmetric Catalysis: Science and Opportunities (Nobel Lecture) (2002) pp. 2008-2022 Wiley-VCH Verlag GmbH, Weinheim, Germany.

A. Miyashita et al; "Synthesis of 2,2'-Bis(diphenylphosphino)-1,1'-binaphthyl (BINAP), an Atropisomeric Chiral Bis(triaryl)phosphine, and it's use in the Rhodium (I)-Catalyzed Asymmetric Hydrogenation of α-(Acylamino)acrylic Acids"; Journal of American Chemical Society (1980) vol. 102, pp. 7932-7934.

M. Burk et al.; "Asymmetric Catalytic Synthesis of β-Branched Amino Acids via Highly Enantioselective Hydrogenation Reactions"; Journal of American Chemical Society (1995) vol. 117, pp. 9375-9376.

G. Zhu et al; "Highly Enantioselective Rh-Catalyzed Hydrogenations with a New Chiral 1,4-Bisphosphine Containing a Cyclic Backbone"; Journal of American Chemical Society (1997) vol. 119, pp. 1799-1800.

(Continued)

*Primary Examiner*—Jerry Lorengo
*Assistant Examiner*—James E McDonough
(74) *Attorney, Agent, or Firm*—Norris McLaughlin & Marcus, P.A.

(57) ABSTRACT

The invention relates to certain chiral transition metal catalysts, to the metal of which at least two structurally different monophosphorus ligands are bonded, at least one of said monophosphorus ligands being chiral. Said chiral transition metal catalysts are suitable as catalysts for use in asymmetric transition metal-catalyzed reactions, providing better enantioselectivities than in cases where only one structurally defined ligand is used.

15 Claims, No Drawings

OTHER PUBLICATIONS

M. Burk et al; "A Convenient Asymmetric Synthesis of α-1-Arylalkylamines through the Enanotioselective Hydrogenation of Enamides"; Journal of American Chemical Society (1996) vol. 118, pp. 5142-5143.

M. T. Reetz, "Combinatorial and Evolution-Based Methods in the Creation of Enantioselective Catalysts"; Agnew. Chem. Int. Ed. (2001) vol. 40, pp. 284-310.

S. Dahmen et al; "Combinatorial Methods for the Discovery and Optimisation of Homogeneous Catalysts"; Synthesis (2001), No. 10, pp. 1431-1449.

M. T. Reetz, et al.; "New Diphosphite Ligands for Catalytic Asymmetric Hydrogenation: The Crucial Role of Conformationally Enantiomeric Diols"; Agnew. Chem. Int. Ed. (1999), vol. 38, No. 1/2; pp. 179-181.

R. Selke, "Carbohydrate phosphinites as chiral ligands for asymmetric synthesis catalyzed by complexes"; Journal of Organometallic Chemistry, 370 (1989) pp. 249-256.

M. T. Reetz, et al.; "Diphosphonites as highly efficient ligands for enantioselective rhodium-catalyzed hydrogenation"; Chem. Commun., (1998) pp. 2077-2078.

M. T. Reetz et al; "Rhodium-catalyzed enantioselective hydrogenation using chiral monophosphonite ligands"; Tetrahedron Letters 41 (2000) pp. 6333-6336.

C. Claver et al.; "Biarylphosphonites: a class of monodentate phosphorus(III) ligands that outperform their chelating analogues in asymmetric hydrogenation catalysis"; Chem. Commun., (2000) pp. 961-962.

M. T. Reetz, et al.; "Highly Enantioselective Rh-Catalyzed Hydrogenation Reactions Based on Chiral Monophosphite Ligands"; Agnew. Chem. Int. Ed. (2000) vol. 39, No. 21; pp. 3889-3890.

I. V. Komarov et al.; "Highly Enantioselective of Not?—Chiral Monodentate Monophosphorus Ligands in the Asymmetric Hydrogenation"; Agnew. Chem. Int. Ed. (2001) vol. 40, No. 7; pp. 1197-1200.

G. Wilkinson; "Comprehensive Coordination Chemistry" Pergamon Press, (1987).

E. N. Jacobsen et al; Comprehensive Asymmetric Catalysis, vol. I-II, Springer, Berlin (1999).

E. Eliel et al., Stereochemistry of Organic Compounds, Wiley & Sons, New York, NY, 1994, pp. 15-20.

\* cited by examiner

MIXTURES OF CHIRAL MONOPHOSPHORUS COMPOUNDS USED AS LIGAND SYSTEMS FOR ASYMMETRIC TRANSITION METAL CATALYSIS

This application is a 371 of PCT/DE2003/003226, filed Sep. 26, 2003.

The present invention includes the surprising finding that mixtures of two or more chiral monophosphorus compounds (i.e. compounds having one phosphorus atom) or mixtures consisting of at least one chiral and at least one achiral monophosphorus compound, constitute excellent ligand systems in asymmetric transition metal catalysis. These are in principle novel processes in the field of enantioselective transition metal catalysis in which known or novel chiral monophosphorus compounds are used. In addition, the chiral transition metal catalysts are of a structurally novel type, since two (or more) different monophosphorus compounds are bonded to the metal, of which at least one is a chiral monophosphorus compound. Such metal complexes have never been mentioned in the literature.

Enantioselective transition metal-catalyzed processes have gained significance industrially in the last 20 years, for example the transition metal-catalyzed asymmetric hydrogenation (B. Cornils, W. A. Herrmann, Applied Homogeneous Catalysis with Organometallic Compounds, Wiley-VCH, Weinheim (1996); W. S. Knowles, Angew. Chem., 114, 2096 (2002); R. Noyori, Angew. Chem., 114, 2108 (2002)). The ligands required for this purpose are frequently chiral phosphorus ligands (P ligands), e.g. phosphines, phosphonites, phosphinites, phosphites or phosphoramidites, which are bonded to the transition metals. Typical examples include rhodium, ruthenium or iridium complexes of optically active diphosphines such as BINAP (A. Miyashita, A. Yasuda, H. Takaya, K. Toriumi, T. Ito, T. Souchi, R. Noyori, J. Am. Chem. Soc., 102, 7932 (1980)), DuPHOS (M. J. Burk, M. F. Gross, J. P. Martinez, J. Am. Chem. Soc., 117, 9375 (1995)), BICP (G. Zhu, P. Cao, Q. Jiang, X. Zhang, J. Am. Chem. Soc., 119, 1799 (1997) and BPE (M. J. Burk, Y. M. Wang, J. R. Lee, J. Am. Chem. Soc., 118, 5142 (1996)). The development of chiral ligands entails a costly process, consisting of design, and trial and error (W. S. Knowles, Angew. Chem., 114, 2096 (2002)). A supplementary search method is what is known as combinatorial asymmetric catalysis, in which libraries of modularly formed chiral ligands or catalyst systems are prepared and tested, as a result of which the probability of finding a hit is increased (M. T. Reetz, Angew. Chem. 113, 292 (2001); S. Dahmen, S. Bräse, Synthesis, 1431 (2001)). A disadvantage in all of these systems is the relatively high preparative complexity in the preparation of large numbers of ligands, and the often insufficient enantioselectivity which is observed in the catalysis. It is therefore still the aim of industrial and academic research to prepare novel, cheap and particularly high-performance ligands by a very simple route.

While most chiral phosphorus ligands are chelating diphosphorus compounds, such as diphosphines (W. S. Knowles, Angew. Chem., 114, 2096 (2002); R. Noyori, Angew. Chem., 114, 2108 (2002)), diphosphites (for example M. T. Reetz, T. Neugebauer, Angew. Chem., 111, 134 (1999)), diphosphinites (for example R. Selke, J. Organomet. Chem., 370, 249 (1989)) or diphosphonites (for example M. T. Reetz, A. Gosberg, R. Goddard, S.-H. Kyung, Chem. Commun. (Cambridge), 2077 (1998)), which bind and stabilize the particular transition metal as a chelate complex, and thus determine the extent of asymmetric induction in the catalysis, it became known sometime ago that certain chiral monophosphonites (for example M. T. Reetz, T. Sell, Tetrahedron Lett., 41, 6333 (2000); C. Claver, E. Fernandez, A. Gillon, K. Heslop, D. J. Hyett, A. Martorell, A. G. Orpen, P. G. Pringle, Chem. Commun. (Cambridge), 961 (2000)), monophosphites (M. T. Reetz, G. Mehler, Angew. Chem., 112, 4047 (2000)) and monophosphoramidites (for example M. van den Berg, A. J. Minnaard, E. P. Schudde, J. van Esch, A. H. M. de Vries, J. G. de Vries, B. L. Feringa, J. Am. Chem. Soc., 122, 11539 (2000)) can likewise be efficient ligands, for example in the rhodium-catalyzed asymmetric hydrogenation of prochiral olefins. Known examples are BINOL-derived representatives, for example the ligands I, II and III. Spectroscopic and mechanistic studies indicate that in each case two monophosphorus ligands are bonded to the metal in the catalysis. Therefore, the metal-ligand ratio is generally 1:2. Some chiral monophosphines of the $R^1R^2R^3P$ type may also be good ligands in transition metal catalysis, even though they are generally expensive (for example W. S. Knowles, Angew. Chem., 114, 2096 (2002)).

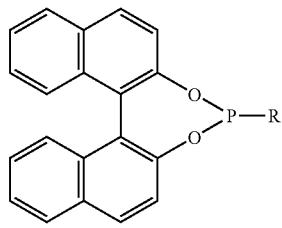

I a) R = CH$_3$
b) R = C$_2$H$_5$
c) R = c-C$_6$H$_{11}$
d) R = C(CH$_3$)$_3$
e) R = C$_6$H$_5$
f) R = Cl

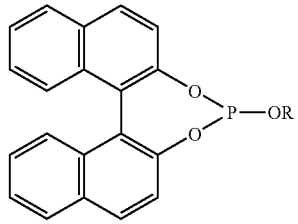

II a) R = CH$_3$
b) R = C$_2$H$_5$
c) R = c-C$_6$H$_{11}$
d) R = C(CH$_3$)$_3$
e) R = C$_6$H$_5$
f) R = 2,6-(CH$_3$)$_2$—C$_6$H$_3$
g) R = CH(CH$_3$)$_2$
h) R = 9-fluorenyl
i) R = CH$_2$C$_6$H$_5$

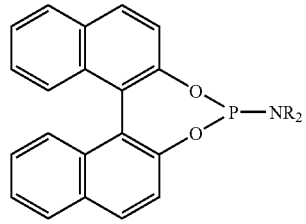

III a) R = CH$_3$
b) R = CH(CH$_3$)$_2$

Monophosphorus ligands of the I-III type are particularly readily available and can be varied very readily owing to the modular structure (I. V. Komarov, A. Börner, Angew. Chem., 113, 1237 (2001)). Variation of the R radical in I, II or III allows a multitude of chiral ligands to be constructed, as a result of which ligand optimization is possible for a given transition metal-catalyzed reaction (for example hydrogenation of a prochiral olefin, ketone or imine or hydroformylation of a prochiral olefin). Unfortunately, here too there exist limits of the method, i.e. many substrates are converted with a moderate or poor enantioselectivity, for example in hydrogenations or hydroformylations. Therefore, there is still a need for cheap and effective chiral ligands for industrial application in transition metal catalysis.

A central constituent of the present invention is the surprising finding that mixtures of two or more monophosphorus compounds of which at least one is chiral lead to higher enantioselectivities in transition metal-catalyzed conversions than the procedure customary hitherto which uses a single, structurally defined monophosphorus ligand. These transition metal catalysts which we have used, in which at least two different monophosphorus ligands (i.e. compounds having one phosphorus atom) are bonded to the metal, at least one monophosphorus ligand being chiral, are novel. These catalysts can be used in a large number of different reaction types for preparing chiral organic compounds from prochiral organic compounds. The optically enriched or pure organic compounds are known to be valuable products or intermediates in industry, for example in the preparation of pharmaceuticals, crop protection agents and fragrances.

Theoretically, the method can always work when at least two monophosphorus ligands (L) are bonded to the metal (M) of the active catalyst MLx in the transition state of the reaction. Such coordination conditions are known for metals of groups IIIb, IVb, Vb, VIb, VIIb, VIIIb, Ib and IIb and for the lanthanides and actinides. For example, in the case of a mixture of two such ligands $L^a$ and $L^b$, three different catalysts present in equilibrium are possible, specifically the traditional homocombinations $ML^aL^a$ and $ML^bL^b$ and the novel heterocombination $ML^aL^b$ (mixed catalyst). In the literature, many examples of homocombinations can be found, in recent times, for example, the monophosphonites I, monophosphites II and the monophosphoramidite III formed modularly from BINOL, each of which frequently (but not always) enable high enantioselectivities in the Rh-catalyzed olefin hydrogenation. In contrast, heterocombinations $ML^aL^b$ have not yet been described as catalysts. Since rapid ligand exchange is generally to be expected, it should barely be possible to generate $ML^aL^b$ in pure form in solution. However, the mixture of the three catalysts can still lead to a higher enantioselectivity when $ML^aL^b$ acts more rapidly and enantioselectivity than the catalysts $ML^aL^a$ and $ML^bL^b$ used in pure form, and the relative amount of the ligands $L^a$ and $L^b$ might likewise play a role.

In order to illustrate this novel principle in the field of asymmetric transition metal catalysis, the enantioselective Rh-catalyzed olefin hydrogenation of a given substrate with an Rh-phosphonite complex derived from I will be described. While traditional use of I where $R=R^1$ affords the ee value x % for enantioselectivity and traditional use of an analog I where $R=R^2$ affords the ee value y %, the use of a mixture of both ligands results in a higher enantioselectivity with the ee value z %, i.e. z>x and z>y. However, this law does not apply to all mixtures. Rather, the increased enantioselectivity is always observed when the correct mixture is selected or the correct selection of the R radicals is made. This is possible rapidly by testing, for example, combinations of different chiral phosphonites, for example of the type I, as mixtures. In the mixture, it is also possible to use more than two different chiral ligands, for example of the type I; preference is given to using two.

In addition to mixtures of chiral monophosphonites, of which the BINOL-derived representatives I constitute only one of many possibilities, mixtures of other chiral monophosphorus ligands may also be used. Examples are mixtures of chiral monophosphites, for example of the type II, or mixtures of monophosphoramidites, for example of the type III. However, it is also possible to use chiral phosphines, phosphiranes, phosphinites, phosphorous tris- and bisamides, phosphoric mono- and diamides, and phosphorous diester fluorides, to name just a few. Indeed, any chiral compound having a phosphorus atom is useful. In practice, there is a wealth of possible phosphorus ligands whose central skeleton is shown by the following formula IV.

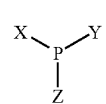

IV

In the formula, the X, Y and Z atoms may each independently be from the group of carbon (C), nitrogen (N), oxygen (O), sulfur (S) or halogen (F, Cl, Br, I). Further atoms or groups of atoms are bonded each independently to the X, Y and Z atoms according to their number of free valences, as, for example, in the examples I, II and III already mentioned. X, Y and Z may also be connected together by the bonded atoms or groups of atoms, and X—P—Y may also be part of an aromatic system, in which case X is then bonded to P by a double bond and there is no substituent Z.

The following combinations of substituents on IV are mentioned by way of example:
a) X=Y=Z=C
b) X=Y=C; Z=N
c) X=Y=C; Z=O
d) X=Y=C; Z=S
e) X=Y=C; Z halogen (F, Cl, Br or I)
f) X=C; Y=Z=N
g) X=C; Y=Z=O
h) X=C; Y=Z=S
i) X=C; Y=N; Z=O
j) X=Y=Z=N
k) X=Y=N; Z=O
l) X=Y=N; Z=S
m) X=Y=N; Z=halogen (F, Cl, Br or I)
n) X=N; Y=Z=O
o) X=N; Y=Z=S
p) X=N; Y=O; Z=halogen (F, Cl, Br or I)
q) X=Y=Z=O
r) X=Y=O; Z=alogen (F, Cl, Br or I)
s) X=Y=Z=S Further examples of representatives are analogs of I, II and III in which the axially chiral building block BINOL is replaced by derivatives, substituted biphenols or by other chiral diols. Specific representatives are, for example, 5,5'-dichloro-6,6'-dimethoxy-2,2'-biphenol, hydrobenzoin, TADDOL and diols derived from carbohydrates. However, these are just a few possible examples whose mention in no way restricts the extent of the possibilities. Since the ligands IV are formed modularly, this means that the particular building blocks are, for example, chiral alcohols, chiral diols, chiral amines, chiral diamines or chiral amino alcohols, to name just the most important possibilities. In the examples which follow, the absolute chirality is not illustrated. However, it is self-evident that any ligand can be used in any possible configuration. The ligands are used in an enantiomerically pure or enriched form. Preference is given to utilizing enantiomerically pure ligands.

Typical examples of chiral ligands IVa are V and VI, which have central and axial chirality respectively:

V

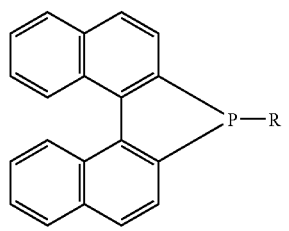
VI (R = alkyl, aryl, alkoxy, amino, halogen)

Typical examples of chiral ligands IVb are VII and VIII:

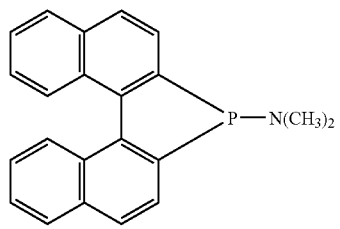
VII

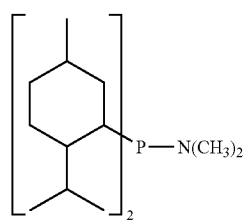
VIII

Typical examples of chiral ligands IVc are IX and X:

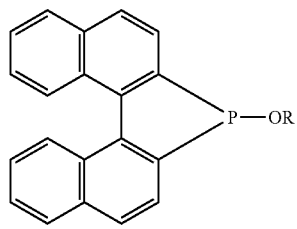
IX (R = alkyl, aryl)

-continued

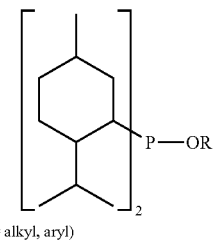
X (R = alkyl, aryl)

Typical examples of chiral ligands IVd are the thio analogs of IX and X.

Typical examples of chiral ligands IVe are XI and XII:

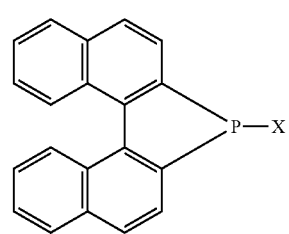
XI (X = F, Cl, Br or I)

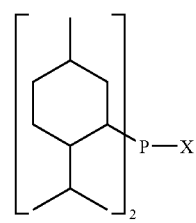
XII (X = F, Cl, Br or I)

Typical examples of chiral ligands Ivf are XIII and XIV:

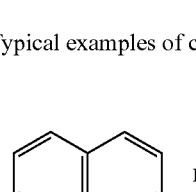
XIII (R = alkyl, aryl; R' = alkyl, aryl, sulfonyl)

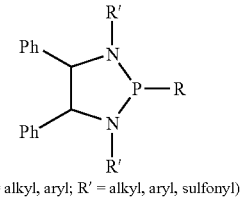
XIV (R = alkyl, aryl; R' = alkyl, aryl, sulfonyl)

Typical examples of chiral ligands IVg and IVh are compounds I and the thio analogs.

Typical examples of chiral ligands IVi are XV and XVI:

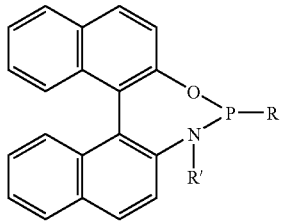

XV (R = alkyl, aryl; R' = alkyl, aryl, sulfonyl)

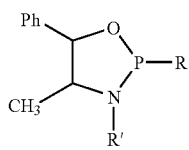

XVI (R = alkyl, aryl; R' = alkyl, aryl, sulfonyl)

Typical examples of chiral ligands IVj are XVII and XVIII:

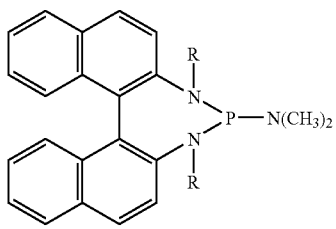

XVII (R = alkyl, aryl, sulfonyl)

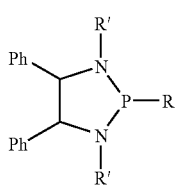

XVIII (R = alkyl, aryl; R' = alkyl, aryl, sulfonyl)

Typical examples of chiral ligands IVk are XIX and XX:

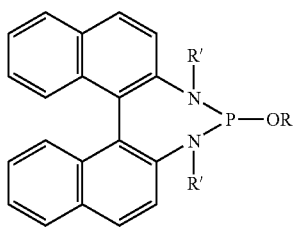

XIX (R = alkyl, aryl; R' = alkyl, aryl, sulfonyl)

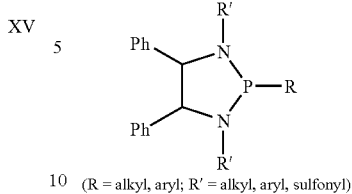

XX (R = alkyl, aryl; R' = alkyl, aryl, sulfonyl)

Typical examples of chiral ligands IVl are the thio analogs of XIX and XX.

Typical examples of chiral ligands IVm are XXI and XXII:

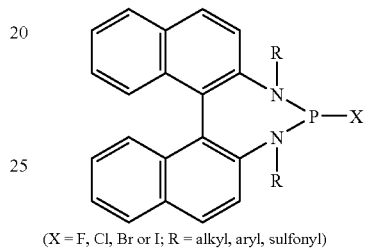

XXI (X = F, Cl, Br or I; R = alkyl, aryl, sulfonyl)

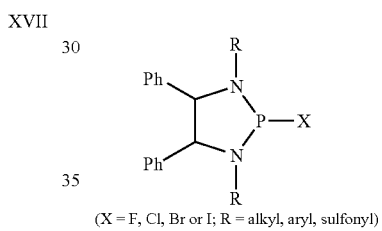

XXII (X = F, Cl, Br or I; R = alkyl, aryl, sulfonyl)

Typical examples of chiral ligands IVn and IVo are III and the thio analogs of III respectively.

Typical examples of chiral ligands IVp are XXIII and XXIV:

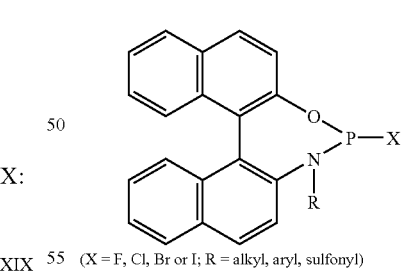

XXIII (X = F, Cl, Br or I; R = alkyl, aryl, sulfonyl)

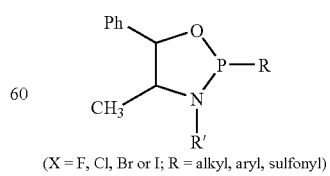

XXIV (X = F, Cl, Br or I; R = alkyl, aryl, sulfonyl)

Typical examples of chiral ligands IVq and IVs are II and the thio analogs of II, respectively.

Typical examples of chiral ligands IVr are XXV and XXVI:

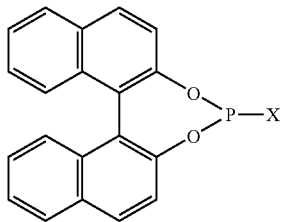

XXV (X = F, Cl, Br or I)

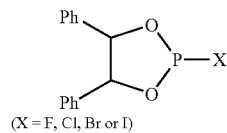

XXVI (X = F, Cl, Br or I)

The underlying principle of the invention does not only apply when the chiral phosphorus ligands belong to the same substance class. An increase in the enantioselectivity is observed even when the mixture is of two (or more) chiral monophosphorus ligands which belong to different classes of phosphorus compounds IV.

A second variant of the invention likewise includes the mixture of two different phosphorus ligands, one of which (as described above) includes chirality, but the other is achiral. The use of a correct combination of a chiral ligand IV and an achiral analog IV leads in transition metal catalysis even in such cases surprisingly to a higher enantioselectivity than in the case of use of the relevant chiral ligand alone. In some cases, such a combination can even be used to reverse the direction of enantioselectivity.

The achiral phosphorus ligands can likewise be described correspondingly by the general formula IV. They are thus, for example, achiral phosphines, phosphinites, phosphonites, phosphorous tris- and bisamides, phosphoric mono- and diamides, to name just a few. Representatives where X=Y=Z=halogen, i.e. PF$_3$, PCl$_3$, PBr$_3$ or PI$_3$, and also thiophosphites P(SR)$_3$, phosphine oxides, phosphine sulfides, iminophosphoranes, phosphiranes and phosphinines are also useful.

As far as the preparation of the catalysts or precatalysts is concerned, the procedure known in the literature which is used typically to prepare traditional homocombinations M(L$^a$)n is useful. This means that the particular ligands mixture is combined with a suitable transition metal complex. The transition metal complexes may be common salts such as MX$_n$ (X=F, Cl, Br, I, BF$_4$, ClO$_4$, RCO$_2$, RSO$_3$ acac), for example [Rh(OAc)$_2$]$_2$, Rh(acac)$_3$, Cu(CF$_3$SO$_3$)$_2$, CuBF$_4$, Ag(CF$_3$SO$_3$), Au(CO)Cl, In(CF$_3$SO$_3$)$_3$, Fe(ClO$_4$)$_3$, NiCl$_2$(COD) (COD=1,5-cyclooctadiene), Pd(OAc)$_2$, [C$_3$H$_5$PdCl]$_2$, PdCl$_2$(CH$_3$CN)$_2$ or La(CF$_3$SO$_3$)$_3$, to name just a few. However, they may also be metal complexes which bear ligands including olefins, dienes, pyridine, CO or NO (to name just a few). The latter are displaced fully or partly by the reaction with the phosphorus ligands. Cationic metal complexes may likewise be used. Those skilled in the art know a multitude of possibilities (G. Wilkinson, Comprehensive Coordination Chemistry, Pergamon Press, Oxford (1987); B. Cornils, W. A. Herrmann, Applied Homogeneous Catalysis with Organometallic Compounds, VCH, Weinheim (1996)). Common examples are Rh(COD)$_2$BF$_4$, [(cymene)RuCl$_2$]$_2$, (pyridine)$_2$ Ir(COD)BF$_4$, Ni(COD)$_2$, (TMEDA)Pd(CH$_3$)$_2$ (TMEDA=N,N,N',N'-tetramethylenediamine), Pt(COD)$_2$, PtCl$_2$(COD) or [RuCl$_2$(CO)$_3$]$_2$, to name just a few. The metals include those of groups IIIb, IVb, Vb, VIb, VIIb, VIII, Ib and IIb of the periodic table, and lanthanides and actinides.

For illustration and for verification that the catalysts are structurally novel, the reactions of Rh(COD)$_2$BF$_4$ with the pure (R)-configured phosphonites I (R=CH$_3$) and I (R=C(CH$_3$)$_3$) to form the traditional Rh complexes XXVII and XXVIII and the reaction with a 1:1 mixture of both ligands to form the "mixed" complex XXIX (as well as the complexes XXVII and XXVIII) will be mentioned. The $^1$H, $^{13}$C and $^{31}$P-NMR spectra of the complex XXIX are characteristic of a "mixed" compound, i.e. they differ from the spectra of the conventional complexes XXVII and XXVIII. When the mixture of the complexes XXVII, XXVIII and XXIX is isolated, it is possible by mass spectrometry (ESI-MS) to unambiguously detect all three complexes, XXIX being the main component. As far as practical application is concerned, the "mixed complex" XXIX does not necessarily have to be separated from the pure complexes XXVII and XXVIII, since it is found on the basis of kinetic investigations that the mixture of the three catalysts is more active than the particular homocombinations XXVII and XXVIII. Analogous NMR and ESI-MS analyses of other "mixed" metal catalysts (heterocombinations) likewise prove the unique structure of these complexes and demonstrate that it is a new substance class.

Rh(COD)$_2$BF$_4$ + Ia (R = CH$_3$) ⟶

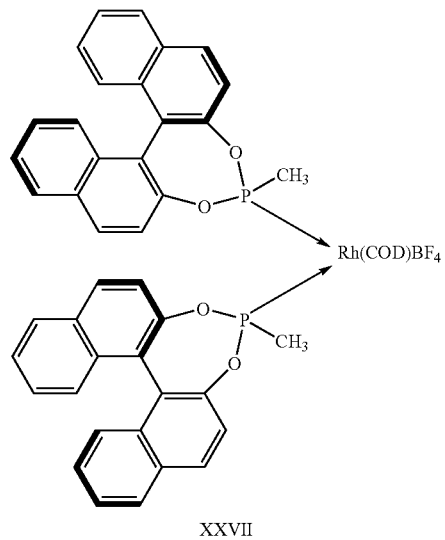

XXVII

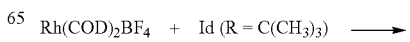

Rh(COD)$_2$BF$_4$ + Id (R = C(CH$_3$)$_3$) ⟶

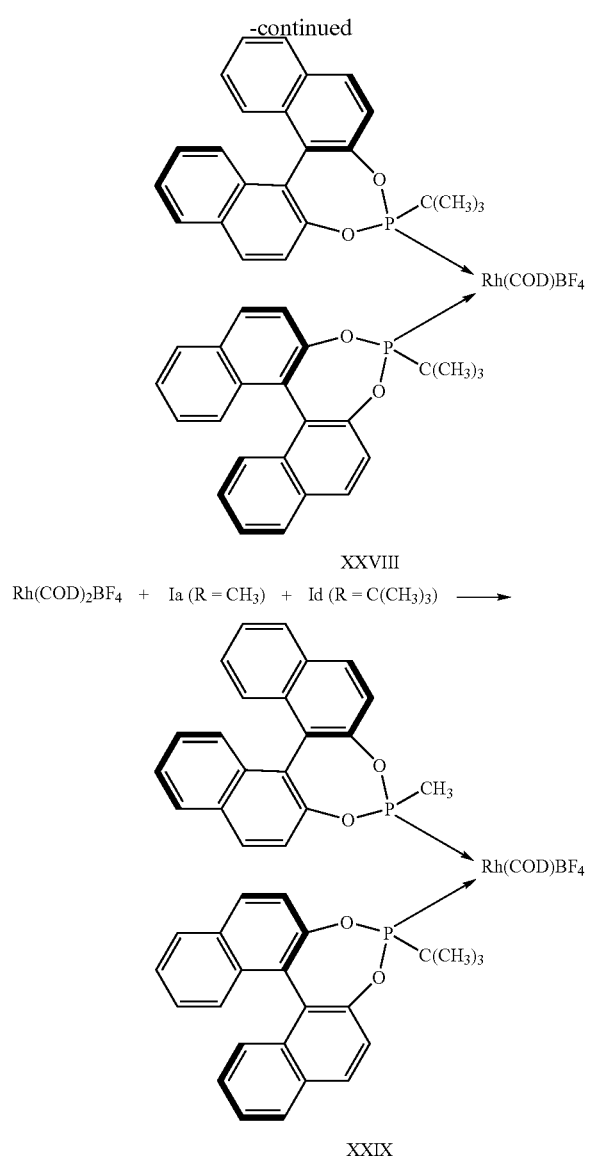

A crucial factor for the invention is the unexpected finding that the overall catalysis profile of the traditional catalysts, for example XXVII and XXVIII, differs greatly from that of the "mixed" complex, for example XXIX. It is found that, for example, in an olefin hydrogenation, the inventive catalyst XXIX affords a distinctly higher enantioselectivity than is achieved when the traditional catalysts XXVII and XXVIII are used. At the same time, a higher rate of reaction is observed. As far as the practical side is concerned, a separation and purification of the "mixed" catalyst XXIX is therefore not necessarily required, i.e. the mixture of XXIX and XXVII/XXVIII can be used, since the high activity of XXIX determines the catalytic result. A further typical example relates to the reaction of $Rh(COD)_2BF_4$ with a 1:1 mixture of Ic and IIa which leads to the mixture of $Rh(Ic)_2(COD)BF_4$, $Rh(IIa)_2(COD)BF_4$ and $Rh(Ic)(IIa)(COD)BF_4$. Here too, investigations show that the heterocombination has different spectroscopic properties than the traditional homocombinations.

The inventive "mixed catalysts" based on heterocombinations of different monophosphorus compounds may contain a plurality of chiral or achiral phosphorus ligands, preferably two different phosphorus ligands. The ratio of the phosphorus ligands relative to one another in the metal complex may be varied as desired. When there are, for example, two different ligands A and B, the relative ratio A:B may preferably be varied between 1:4 and 4:1; particular preference is given to selecting an A:B ratio of approx. 1:1. The ratio of metal to substrate moves within the customary range, i.e. between 1:5 and 1:1 000 000.

The searching of libraries of mixtures of two chiral monophosphorus ligands or of mixtures of one chiral and one achiral phosphorus ligand provides the simple means of finding the best mixed catalyst (heterocombination) for a given transition metal-catalyzed conversion. This procedure is simple and can be performed rapidly with modern instruments which are customary in combinatorial catalysis. These include parallelized reactors and pipetting robots (M. T. Reetz, Angew. Chem., 113, 292 (2001)). However, a sequential procedure is also possible, i.e. one mixture can be tested after another. The inventive use of two (or more) chiral monophosphorus ligands or mixtures of chiral and achiral monophosphorus ligands applies to all transition metal-catalyzed reactions (E. N. Jacobsen, A. Pfaltz, H. Yamamoto, Comprehensive Asymmetric Catalysis, Vol. I-III, Springer, Berlin (1999)), in particular to asymmetric hydrogenations, hydroformylations, hydroborations, hydrosilylations, hydrovinylations, hydroaminations, epoxidations, hydroxylations, aminohydroxylations, substitutions (for example allyl substitutions), Heck, Stille, Suzuki and Negishi couplings, Michael additions, aldol additions, Diels-Alder reactions, cyclopropanations, CH insertion reactions and 1,3-dipolar cycloadditions.

EXAMPLES

Example 1

Rh-Catalyzed Hydrogenation of Methyl N-Acylacrylate Using Ligands of the I, II and III Type

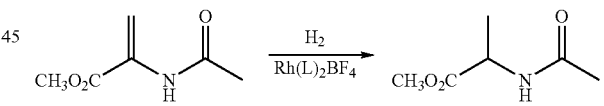

A baked-out 50 ml Schlenk vessel was initially charged under an argon atmosphere with a mixture of 0.6 ml of a 1.7 mM solution of the first ligand and 0.6 ml of a 1.7 mM solution of the second ligand in abs. dichloromethane. This solution was admixed with 0.5 ml of a 2.0 mM solution of $[Rh(COD)_2]BF_4$ in dichloromethane and stirred at room temperature for 5 minutes. Subsequently, 9 ml of a 0.112 M solution of the substrate in dichloromethane were added. The vessel was three times evacuated until the solvent was boiling gently and aerated with hydrogen. At hydrogen pressure 1.3 bar, the mixture was stirred for the duration of the reaction. The conversion was determined by gas chromatography after dilution of the reaction solution.

For the determination of the enantiomeric excess, approx. 1.5 ml of the reaction solution were filtered adsorptively through a little silica gel and analyzed by gas chromatography or by means of HPLC. The experiments were carried out with 20 vessels in parallel.

For comparison, the pure ligands were tested under otherwise identical conditions in the Rh-catalyzed hydrogenation. The results are compiled in table 1. According to these, there are actually several mixed catalysts (heterocombinations) that are distinctly more enantioselective (for example entries 16, 17, 40, 42, 44 and 45) than the analogs formed from traditional pure ligands (entries 1-14).

TABLE 1

Rh-catalyzed hydrogenation of Iva[a]

| Entry | Ligands | ee [%] (config.) |
|---|---|---|
| | Homocombinations | |
| 1 | (R)Ia/(R)Ia | 91.8 (S) |
| 2 | (R)Ib/(R)Ib | 94.4 (S) |
| 3 | (R)Ic/(R)Ic | 92.0 (S) |
| 4 | (R)Id/(R)Id | 93.3 (S) |
| 5 | (R)Ie/(R)Ie | 72.8 (S) |
| 6[b] | (R)If/(R)If | 7.4 (S) |
| 7 | (S)IIa/(S)IIa | 76.6 (R) |
| 8 | (S)IIb/(S)IIb | 83.6 (R) |
| 9 | (R)IIc/(R)IIc | 94.6 (S) |
| 10 | (S)IId/(S)IId | 95.4 (R) |
| 11[c] | (S)IIe/(S)IIe | 78.6 (R) |
| 12[d] | (S)IIf/(S)IIf | 32.4 (R) |
| 13 | (S)IIg/(S)IIg | 94.4 (R) |
| 14 | (S)IIh/(S)IIh | 92.4 (R) |
| | Heterocombinations | |
| 15 | (R)Ia/(R)Ib | 92.6 (S) |
| 16 | (R)Ia/(R)Ic | 97.9 (S) |
| 17 | (R)Ia/(R)Id | 97.8 (S) |
| 18 | (R)Ic/(R)Id | 94.1 (S) |
| 19 | (R)Id/(R)Ie | 75.8 (S) |
| 20 | (R)Id/(R)If | racemic |
| 21 | (R)IIa/(R)IIb | 80.0 (S) |
| 22 | (R)IIa/(R)IIc | 76.6 (S) |
| 23 | (R)IIa/(R)IId | 89.0 (S) |
| 24 | (R)IIa/(R)IIe | 77.4 (S) |
| 25 | (R)IIa/(R)IIf | 84.6 (S) |
| 26 | (R)IIa/(R)IIg | 87.2 (S) |
| 27 | (R)IIb/(R)IIc | 79.0 (S) |
| 28 | (R)IIb/(R)IId | 91.2 (S) |
| 29 | (R)IIb/(R)IIe | 80.8 (S) |
| 30 | (R)IIb/(R)IIg | 90.0 (S) |
| 31 | (R)IId/(R)IIc | 94.2 (S) |
| 32 | (R)IId/(R)IIe | 92.2 (S) |
| 33 | (R)IIe/(R)IIc | 73.6 (S) |
| 34 | (R)IIg/(R)IIc | 94.6 (S) |
| 35 | (R)IIg/(R)IId | 94.8 (S) |
| 36 | (R)IIg/(R)IIe | 91.2 (S) |
| 37 | (R)Ia/(R)IIa | 81.9 (S) |
| 38 | (R)Ia/(R)IIc | 94.4 (S) |
| 39 | (R)Ia/(R)IId | 93.0 (S) |
| 40 | (R)Ic/(R)IIa | 96.4 (S) |
| 41 | (R)Ic/(R)IId | 91.8 (S) |
| 42 | (R)Id/(R)IIa | 98.0 (S) |
| 43 | (R)Id/(R)IIc | 94.6 (S) |
| 44 | (R)Id/(R)IIh | 97.2 (S) |
| 45 | (R)Ic/(R)IIh | 95.6 (S) |

[a]Rh/substrate ratio 1:1000; Rh/P ratio 1:2; solvent: $CH_2Cl_2$; $p(H_2)$: 1.3 bar; T: 20° C.; reaction time: 20 h; conversion: 100%.
[b]Conversion: 1%.
[c]Conversion: 93%.
[d]Conversion: 62%.

Example 2

Rh-Catalyzed Hydrogenation of Methyl Phenyl-N-Acylacrylate Using Ligands of the I Type

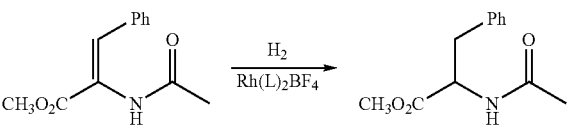

A baked-out 50 ml Schlenk vessel was initially charged under an argon atmosphere with a mixture of 0.6 ml of a 1.7 mM solution of the first ligand and 0.6 ml of a 1.7 mM solution of the second ligand in abs. dichloromethane. This solution was admixed with 0.5 ml of a 2.0 mM solution of $[Rh(COD_2]BF_4$ in dichloromethane and stirred at room temperature for 5 minutes. Subsequently, 9 ml of a 0.112 M solution of the substrate in dichloromethane were added. The vessel was three times evacuated until the solvent was boiling gently and aerated with hydrogen. At hydrogen pressure 1.3 bar, the mixture was stirred for the duration of the reaction. The conversion was determined by gas chromatography after dilution of the reaction solution. For the determination of the enantiomeric excess, approx. 1.5 ml of the reaction solution were filtered adsorptively through a little silica gel and analyzed by gas chromatography or by means of HPLC. The experiments were carried out with 20 vessels in parallel.

The measured enantioselectivities at 100% conversion are as follows: (R)Ia/(R)Ic: ee=9.6.7% (S); (R)Ia/(R)Id: ee=99.2% (S): (R)Ib/(R)Id: ee=94.6% (S) compared to (R)Ia/(R)Ia: ee=89.9% (S); (R)Ib/(R)Ib: ee=89.2% (S); (R)Id/(R)Id: ee=69.1% (S).

Example 3

Rh-Catalyzed Hydrogenation of 1-N-Acylaminostryene Using Ligands of the I and II type

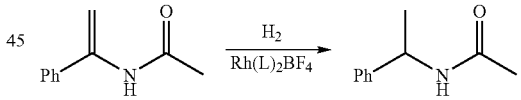

Analogously to the method in example 1, a mixture of 0.5 ml of a 2 mM solution of $Rh(COD)_2BF_4$ in dry $CH_2Cl_2$, 0.25 ml of a 4 mM solution of a phosphonite I and 0.25 ml of a 4 mM solution of a second phosphonite I in $CH_2Cl_2$ were prepared. This led to change in the color from orange to yellow. After 1-N-ayclaminostyrene (0.5 mM) in 1 ml of $CH_2Cl_2$ had been added, the reaction solution was stirred at 30° C. and 1.5 bar of $H_2$ pressure for 22 hours. The GC analysis gives the conversion and the ee value.

Rh-catalyzed hydrogenation of 1-N-acetamidostyrene

| Entry | Ligands | ee (%)configuration |
|---|---|---|
| | Homocombinations | |
| 1 | (R)Ia/(R)Ia | 75.6 (S) |
| 2[b] | (R)Id/(R)Id | 83.0 (S) |

-continued

| Entry | Ligands | ee (%)configuration |
|---|---|---|
| 3 | (R)IIa/(R)IIa | 76.0 (S) |
| 4 | (R)IIc/(R)IIc | 84.8 (S) |
| 5 | (R)IIe/(R)IIe | 85.4 (S) |
| 6 | (R)IIi/(R)IIi | 91.4 (S) |
| | Heterocombinations | |
| 7[c] | (R)Ia/(R)Id | 96.1 (S) |
| 8 | (R)IIa/(R)Id | 95.0 (S) |
| 9 | (R)IIe/(R)IIc | 88.6 (S) |
| 10 | (R)IIi/(R)Id | 97.4 (S) |

[a]Rh/substrate ratio 1:500, rest as table 1
[b]Conversion: 13%
[c]Conversion: >95%

Example 4

Rh-Catalyzed Hydrogenation of 1-N-Acylamino-1-p-Chlorophenylethylene

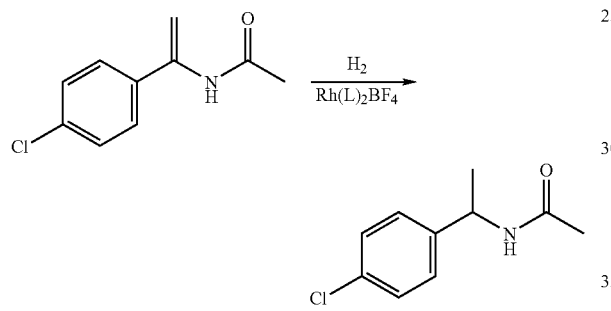

The hydrogenations are effected analogously to the method in example 3. The measured enantioselectivities at >95% conversion are as follows: (R)Ia/(R)Id: ee=95.0% (S) compared to (R)Ia/(R)Ia: ee=73.0% (S) and (R)Id/(R)Id: ee=16.2% (S), conversion 79%.

Example 5

Variation of the Ratio of the Two Phosphorus Ligands Ia and Id in the Rh-Catalyzed Hydrogenation of 1-N-Acylaminostyrene The hydrogenations were carried out as in example 3, but with variation of the relative ratio of Ia and Id. The Rh:P ratio was kept constant at 1:2 and the Rh:substrate ratio at 1:500. The enantioselectivities determined by means of GC at conversions of >95% are compiled in table 2.

TABLE 2

Influence of the Ia:Id ratio on the enantioselectivity of the hydrogenation of VIa[a]

| Entry | Ligands (R)Ia/(R)Id | ee [%] (config.) |
|---|---|---|
| 1[b] | 1:5 | 95.4 (S) |
| 2 | 1:3 | 97.4 (S) |
| 3 | 1:2 | 97.2 (S) |
| 4 | 1:1 | 96.4 (S) |
| 5 | 2:1 | 88.8 (S) |

TABLE 2-continued

Influence of the Ia:Id ratio on the enantioselectivity of the hydrogenation of VIa[a]

| Entry | Ligands (R)Ia/(R)Id | ee [%] (config.) |
|---|---|---|
| 6 | 3:1 | 85.0 (S) |
| 7 | 5:1 | 81.2 (S) |

[a] In all cases, the Rh/((R)Ia/(R)Id) ratio was 1:2 and the Rh/substrate ratio 1:500. Solvent: $CH_2Cl_2$; $p(H_2)$: 1.5 bar; T: 20° C.; reaction time: 1 h; conversion: 100%.
[b] Conversion: 95%.

Example 6

Rh-Catalyzed Hydrogenation of 1-N-Acylamino-1-Naphthylethylene Using Ligands of the I type

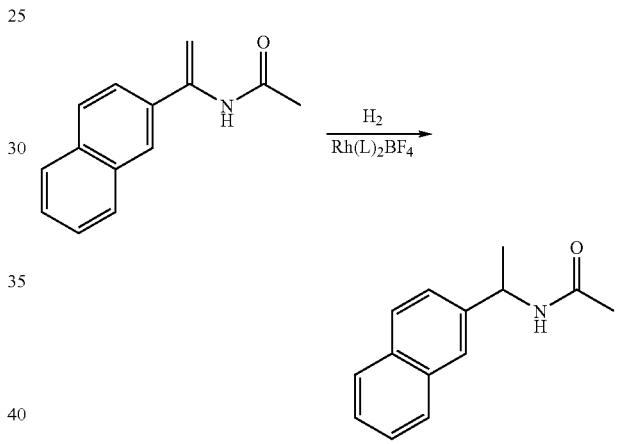

The hydrogenations were effected analogously to the method in example 3. The measured enantioselectivities at >95% conversion are as follows: (R)Ia/(R)Id: ee=97.0% (S) compared to (R)Ia/(R)Ia: ee=78.2% (S) and (R)Id/(R)Id: ee=<3% (S), conversion 35%.

Example 7

Rh-Catalyzed Hydrogenation of Dimethyl Itaconate Using Ligands of the I type

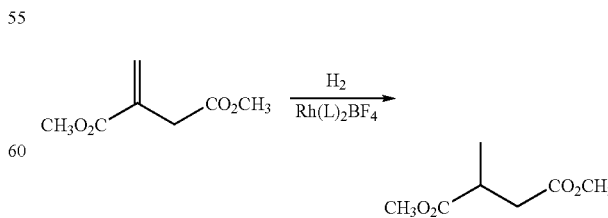

The hydrogenation was effected analogously to the method in example 1. The enantioselectivities determined by means of GC at quantitative conversion are compiled in table 3.

TABLE 3

| | Rh-catalyzed hydrogenation of VIII[a] | |
|---|---|---|
| Entry | Ligands | ee [%] (config.) |
| | Homocombinations | |
| 1 | (R)Ia/(R)Ia | 90.2 (R) |
| 2 | (R)Ib/(R)Ib | 71.4 (R) |
| 3 | (R)Ic/(R)Ic | 21.9 (R) |
| 4 | (R)Id/(R)Id | 57.3 (R) |
| 5 | (R)Ie/(R)Ie | 28.8 (R) |
| | Heterocombinations | |
| 6 | (R)Ia/(R)Ib | 82.4 (R) |
| 7 | (R)Ia/(R)Ic | 88.6 (R) |
| 8 | (R)Ia/(R)Id | 96.4 (R) |
| 9 | (R)Ib/(R)Id | 92.2 (R) |
| 10 | (R)Ic/(R)Id | 69.1 (R) |
| 11 | (R)Ic/(R)Ie | 50.0 (R) |
| 12 | (R)Id/(R)Ie | 57.4 (R) |

[a]In all cases, the Rh/P ratio was 1:2 and the Rh/substrate ratio 1:1000. Solvent: $CH_2Cl_2$; p($H_2$): 1.3 bar; T: 20° C., reaction time: 20 h; conversion: 100%.

The quantitative hydrogenation may also be carried out with reduction of the Rh/substrate ratio under otherwise identical conditions. At Rh: substrate=1:6000, the ee value is 95.8% (R); at 1:10 000, the ee value is 95.4% (R); at 1:20 000, the ee value is 94.6% (R).

Example 8

Rh-Catalyzed Hydrogenation Of Methyl N-acylaminoacrylate Using Chiral Phosphonites I, Phosphites II, Phosphoramidites III and Achiral Monophosphorus Ligands

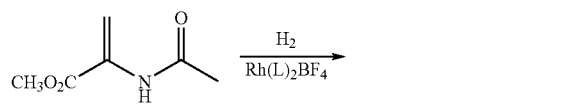

The conditions of the hydrogenations were as selected in example 1, except that a chiral phosphorus ligand (compound I or II) and an achiral phosphorus ligand (compound XXX or XXXI) were used in a ratio of 1:1.

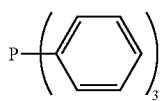
XXX

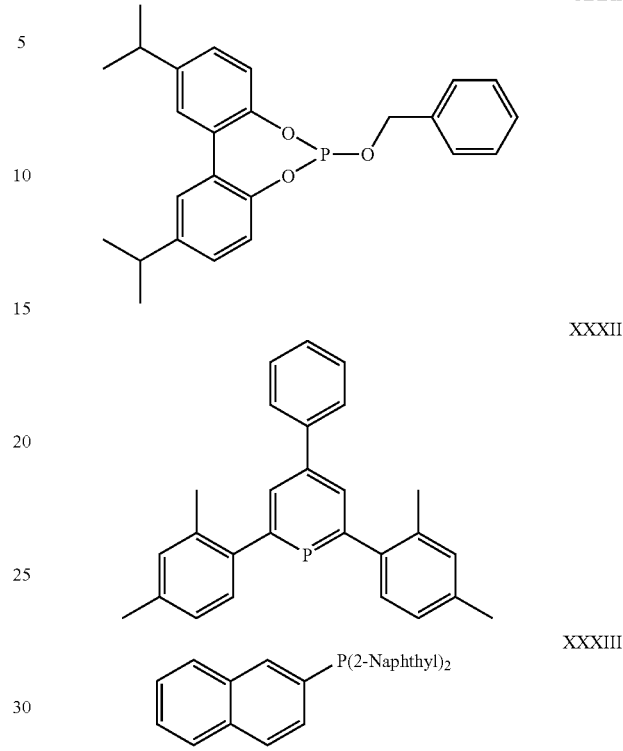

The results of the hydrogenation with reversal of the enantioselectivity at quantitative conversion are as follows:

| Entry | Ligands | ee (%) configuration |
|---|---|---|
| 1 | (R)Ia/XXX | 19.6 (R) |
| 2 | (R)IIa/XXX | 10.0 (R) |
| 3 | (R)IId/XXX | 45.4 (R) |
| 4 | (R)Ia/XXXII | 58.6 (R) |
| 5 | (R)Id/XXXII | 52.6 (R) |
| 6 | (R)IId/XXXIII | 34.8 (R) |

Rh/substrate ratio 1:1000; Rh/P ratio 1:2; solvent: $CH_2Cl_2$; p($H_2$): 1.3 bar; T: 20° C.; reaction time: 20 h; conversion: 100%.

Example 9

Preparation and Characterization of the Catalyst System Rh[Ia][Id][COD]$BF_4$ +Rh[Ia]$_2$[COD]$BF_4$+Rh[Id]$_2$[COD]$BF_4$ The mixture of (R)Ia (13.2 mg; 0.04 mmol) and (R)Id (14.9 mg; 0.04 mmol) in $CD_2Cl_2$ (1 ml) was treated with Rh[COD]$_2$ $BF_4$ (16.2 mg; 0.04 mmol) in $CD_2Cl_2$ (1 ml). The $^1$H, $^{13}$C and $^{31}$P NMR spectra show the presence of the two homocombinations Rh[(R) Ia]$_2$[COD]$BF_4$ (XXVII) and Rh[(R)Id]$_2$ [COD]$BF_4$ (XXVIII) and the heterocombination Rh[(R)Ia] [(R)Id]$BF_4$ (XXIX) in a ratio of about 20:20:60. The characteristic peaks and distributions in the $^{31}$P spectrum are as follows:

| | $\delta_p$ (Ia) | $\delta_p$ (Id) | $J_{RhP}$, Hz | $J_{PP}$, Hz | % |
|---|---|---|---|---|---|
| $^{31}$P NMR (121.5 MHz, 223 K, CD$_2$Cl$_2$, rel. ext. 85% H$_3$PO$_4$): | | | | | |
| Rh[(R)Ia]$_2$[COD]BF$_4$ | 189.8 | | 206 | | 18 |
| Rh[(R)Id]$_2$[COD]BF$_4$ | | 204.8 | 207 | | 23 |
| Rh[(R)Ia][(R)Id][COD]BF$_4$ (1st isomer) | 187.0 | 208.3 | 208, 210 | 38 | 15 |
| Rh[(R)Ia][(R)Id][COD]BF$_4$ (2nd isomer) | 202.4, 201.8 | | 201, 212 | 40 | 44 |

Example 10

Preparation, Isolation and Characterization of the Catalyst System Rh[Ia][Id][COD]BF$_4$+Rh[Ia]$_2$[COD]BF$_4$+Rh[Id]$_2$[COD]BF$_4$ by means of ESI-MS A mixture of (R)Ia (32.6 mg; 0.1 mmol) and (R)Id (36.9 mg; 0.1 mmol) in CH$_2$Cl$_2$ (20 ml) was admixed at −78° C. with Rh[COD]$_2$BF$_4$ (40.7 mg; 0.1 mmol) in CH$_2$Cl$_2$ (5 ml). After warming to room temperature, the solvent was concentrated to 5 ml and a yellow solid was precipitated with 15 ml of pentane. This was washed three times with pentane and dried under reduced pressure. In the ESI-MS spectrum, fragments of the complexes described in example 9 can be detected, the complex XXIX of the heterocombination constituting the main component. The $^{31}$P NMR spectrum in CD$_2$Cl$_2$ shows the same signals as have already been described and assigned in example 9.

Rh[(R)Ia]$_2$[COD]BF$_4$ (XXVII): MS(ESI/pos. in CH$_2$Cl$_2$): m/z=763 [M$^+$—BF$_4$—COD].

Rh[(R)Id]$_2$[COD]BF$_4$ (XXVIII): MS(ESI/pos. in CH$_2$Cl$_2$): m/z=847 [M$^+$—BF$_4$—COD].

Rh[(R) Ia] [(R) Id] [COD]BF$_4$ (XXIX): MS(ESI/pos. in CH$_2$Cl$_2$): m/z=805 [M$^+$—BF$_4$—COD].

Example 11

Analysis of A Mixture of Rh[Ia]$_2$[COD]BF$_4$ and Rh[Id]$_2$[COD]BF$_4$

A solution of Rh[Ia]$_2$[COD]BF$_4$ (3.3 mg; 0.0034 mmol; 0.5 ml of CD$_2$Cl$_2$) and a solution of Rh[Id]$_2$[COD]BF$_4$ (3.5 mg; 0.0034 mmol; 0.5 ml of CD$_2$Cl$_2$) were mixed. The mixture was analyzed by $^{31}$P NMR spectroscopy. With reference to the signals (analogously to example 9), it is found that the same components Rh[(R)Ia]$_2$[COD]BF$_4$ (XXVII), Rh[(R)Id]$_2$[COD]BF$_4$ (XXVIII) and Rh[(R)Ia][(R)Id]BF$_4$ (XXIX) are present as in example 9.

Example 12

Preparation, Isolation and Characterization of the Catalyst System Rh[Ia][Ic][COD]BF$_4$+Rh[Ia]$_2$[COD]BF$_4$+Rh[Ic]$_2$[COD]BF$_4$ by means of ESI-MS A mixture of (R)Ia (29.4 mg; 0.09 mmol) and (R)Ic (35.5 mg; 0.09 mmol) in CH$_2$Cl$_2$ (20 ml) was admixed at −78° C. with Rh[COD]$_2$BF$_4$ (36.5 mg; 0.09 mmol) in CH$_2$Cl$_2$ (5 ml). After warming to room temperature, the solvent was concentrated to 5 ml and a yellow solid was precipitated with 15 ml of pentane. This was washed three times with pentane and dried under reduced pressure. In the ESI-MS spectrum, the following fragments can be detected:

Rh[(R)Ia]$_2$[COD]BF$_4$: MS(ESI/pos. in CH$_2$Cl$_2$): m/z=763 [M$^+$—BF$_4$—COD].

Rh[(R)Ic]$_2$[COD]BF$_4$: MS(ESI/pos. in CH$_2$Cl$_2$): m/z=897 [M$^+$—BF$_4$—COD—2H]

Rh[(R)Ia][(R)Ic][COD]BF$_4$: MS(ESI/pos. in CH$_2$Cl$_2$): m/z=831 [M$^+$—BF$_4$—COD]

Example 13

Preparation, Isolation and Characterization of the Catalyst System Rh[IIa][IC][COD]BF$_4$+Rh[IIa]$_2$[COD]BF$_4$+Rh[Ic]$_2$[COD]BF$_4$ by means of ESI-MS A mixture of (R)IIa (44.6 mg; 0.13 mmol) and (R)Ic (51.8 mg; 0.13 mmol) in CH$_2$Cl$_2$ (20 ml) was admixed at −78° C. with Rh[COD]$_2$BF$_4$ (52.8 mg; 0.13 mmol) in CH$_2$Cl$_2$ (5 ml). After warming to room temperature, the solvent was concentrated to 5 ml and a yellow solid was precipitated with 15 ml of pentane. This was washed three times with pentane and dried under reduced pressure. In the ESI-MS spectrum, the following fragments can be detected:

Rh[(R)IIa]$_2$[COD]BF$_4$: MS(ESI/pos. in CH$_2$Cl$_2$): m/z=795 [M$^+$—BF$_4$—COD].

Rh[(R)Ic]$_2$[COD]BF$_4$: MS(ESI/pos. in CH$_2$Cl$_2$): m/z=897 [M$^+$—BF$_4$—COD—2H].

Rh[(R)IIa][(R) IC][COD]BF$_4$: MS(ESI/pos. in CH$_2$Cl$_2$): m/z=845 [M$^+$—BF$_4$—COD—2H].

What is claimed is:

1. A chiral transition metal catalyst comprising at least two constitutionally different monophosphorus ligands bonded to a transition metal, at least one monophosphorus ligand being chiral.

2. A catalyst as claimed in claim 1, wherein precisely one monophosphorus ligand is chiral.

3. A catalyst as claimed in claim 1, wherein the monophosphorus ligands are each independently of the A type. are chiral.

4. A catalyst as claimed in claim 1, wherein the monophosphorus ligands are each independently of the A type

A where the X, Y and Z atoms are each independently from the group of carbon, nitrogen, oxygen, sulfur or halogen, to which, according to their number of free valences, further atoms or groups of atoms are bonded independently of one another, where X, Y and Z may also be connected to one another by the bonded atoms or groups of atoms, where X—P—Y may also be part of an aromatic system, in which case X is bonded to P by a double bond and there is no substituent Z.

5. A catalyst as claimed in claim 1, wherein the monophosphorus ligands are phosphines, phosphites, phosphonites, phosphinites, phosphorous triamides, phosphorous monoester diamides, phosphorous diester amides, phosphonous diamides, phosphinous amides, phosphonous monoester amides, phosphorous halides, phosphorous diamide halides, thiophosphites, thiophosphorous triesters, thiophosphorous monoester diamides or thiophosphorous diesteramides.

6. A catalyst as claimed in claim 1, wherein the chiral ligands are monophosphorus compounds of the B, C or D type

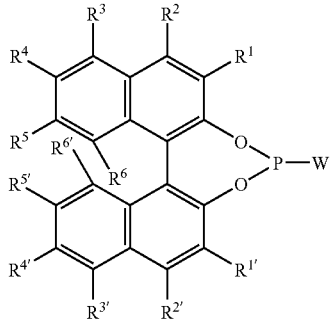

B

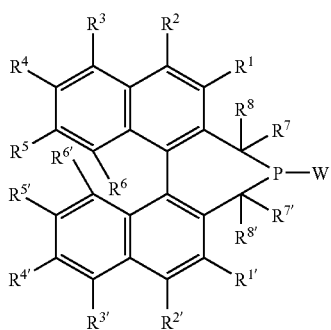

C

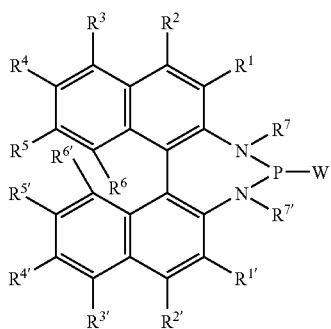

D where W is carbon, nitrogen, oxygen, sulfur or halogen, and further atoms or groups of atoms are bonded to W according to its number of free valences, and where the $R^1$, $R^2$, $R^3$, $R^4$, $R^5$, $R^6$, $R^7$, $R^8$, $R^{1'}$, $R^{2'}$, $R^{3'}$, $R^{4'}$, $R^{5'}$, $R^{6'}$, $R^{7'}$ and $R^{8'}$ radicals are each independently from the group of hydrogen, halogen, saturated and unsaturated, linear and branched $C_1$-$C_{50}$ alkyl, $C_1$-$C_{50}$ aryl, $C_1$-$C_{50}$ heteroaryl, alkynyl, silyl, nitro, nitrile, ester, carboxyl, carbonyl, amide, amine, hydroxyl, alkoxy, sulfide and selenide groups, where $R^1$, $R^2$, $R^3$, $R^4$, $R^5$, $R^6$, $R^7$, $R^8$, $R^{1'}$, $R^{2'}$, $R^{3'}$, $R^{4'}$, $R^{5'}$, $R^{6'}$, $R^{7'}$ and $R^{8'}$ in turn bear further substituents or may be functionalized, and where one or more carbon atoms of the binaphthyl skeletons may each independently be replaced by the heteroatoms Si, O, N or S.

7. A catalyst as claimed in claim 1, wherein the chiral ligands are monophosphorus compounds of the E, F or G type

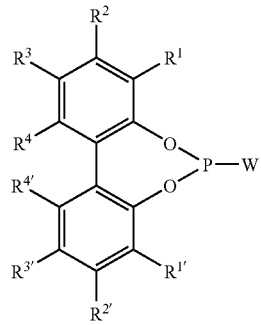

E

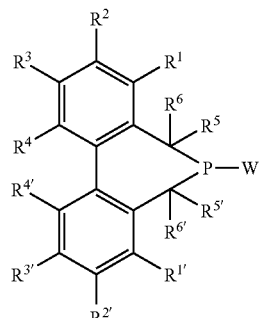

F

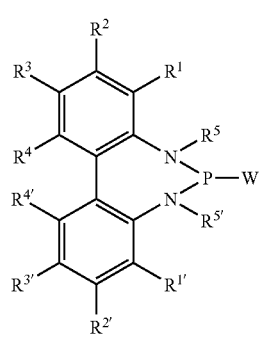

G where W is carbon, nitrogen, oxygen, sulfur or halogen, and further atoms or groups of atoms are bonded to W according to its number of free valences, and where the $R^1$, $R^2$, $R^3$, $R^4$, $R^5$, $R^6$, $R^{1'}R^{2'}$, $R^{3'}$, $R^{4'}$, $R^{5'}$ and $R^{6'}$ radicals are each independently from the group of hydrogen, halogen, saturated and unsaturated, linear and branched $C_1$-$C_{50}$ alkyl, $C_1$-$C_{50}$ aryl, $C_1$-$C_{50}$ heteroaryl, alkynyl, silyl, nitro, nitrile, ester, carboxyl, carbonyl, amide, amine, hydroxyl, alkoxy, sulfide and selenide groups, where $R^1$, $R^2$, $R^3$, $R^4$, $R^5$, $R^6$, $R^{1'}$, $R^{2'}$, $R^{3'}$, $R^{4'}$, $R^{5'}$ and $R^{6'}$ in turn bear further substituents or may be functionalized, and where one or more carbon atoms of the biphenyl skeletons may each independently be replaced by the heteroatoms Si, O, N or S.

8. A catalyst as claimed in claim 1, wherein at least one achiral ligand is a monophosphorus compound of the H-T type

PR¹₂R²

P(OR¹)₂(OR²)

P(NR¹R²)₃

P(SR¹)₂(SR²)

R¹OP(NR²R³)₂

(R¹O)₂P(NR²R³)

O=P(OR¹)₂(OR²)

O=P(NR¹R²)₂(NR³R⁴)

S=P(OR¹)₂(OR²)

S=P(NR¹R²)₂(NR³R⁴)

R—N=P(OR¹)₂(OR²)

R—N=P(NR¹R²)₂(NR³R⁴)

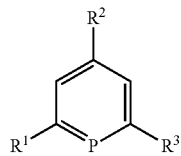

where the $R^1$, $R^2$, $R^3$ and $R^4$ radicals are each independently from the group of hydrogen, halogen, saturated and unsaturated, linear and branched $C_1$-$C_{50}$ alkyl, $C_1$-$C_{50}$ aryl, $C_1$-$C_{50}$ heteroaryl, alkynyl, silyl, nitro, nitrile, ester, carboxyl, carbonyl, amide and selenide groups, where $R^1$, $R^2$, $R^3$ and $R^4$ in turn bear further substituents, and may be functionalized or bridged.

9. A catalyst as claimed in claim 1, wherein the transition metal is a metal of groups IIIb, IVb, Vb, VIb, VIIb, VIII, Ib or IIb of the periodic table or a lanthanide or actinide.

10. A catalyst as claimed in claim 9, wherein the transition metal is Rh, Ir, Ru, Ni, Pd or Pt.

11. A catalyst as claimed in claim 3, wherein the chiral monophosphorus ligands used are at least two ligands of the

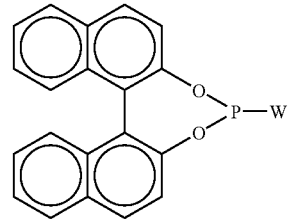

type where W is each independently $CH_3$, $C(CH_3)_3$, $C$—$C_6H_{11}$ or $OCH_3$.

12. A process for catalytically preparing chiral organic compounds, comprising conducting a chemical reaction of prochiral organic compounds in the presence of a transition metal catalyst as claimed in claim 1.

13. The process as claimed in claim 12, wherein the chemical reaction is a hydrogenation.

14. The process as claimed in claim 12, wherein the chemical reaction is a hydroformylation.

15. The process as claimed in claim 12, wherein the chemical reaction is a hydroboration, hydrosilylation, hydrovinylation, hydroamination, epoxidation, hydroxylation, aminohydroxylations, substitution, allyl substitution, Heck coupling, Stille coupling, Suzuki coupling, Negishi coupling, Michael addition, aldol addition, Diels-Alder reaction, cyclopropanation, CH insertion reaction or 1,3-dipolar cycloaddition.

* * * * *